United States Patent
Imagawa et al.

(10) Patent No.: US 9,526,469 B2
(45) Date of Patent: Dec. 27, 2016

(54) X-RAY DIAGNOSTIC APPARATUS

(71) Applicant: TOSHIBA MEDICAL SYSTEMS CORPORATION, Otawara-Shi (JP)

(72) Inventors: Kazuo Imagawa, Nasushiobara (JP); Masanori Matsumoto, Nasushiobara (JP); Toshiya Waku, Yaita (JP); Keisuke Nakamura, Utsunomiya (JP); Naotaka Sato, Otawara (JP)

(73) Assignee: Toshiba Medical Systems Corporation, Otawara-shi (JP)

( * ) Notice: Subject to any disclaimer, the term of this patent is extended or adjusted under 35 U.S.C. 154(b) by 262 days.

(21) Appl. No.: 14/144,870

(22) Filed: Dec. 31, 2013

(65) Prior Publication Data

US 2014/0112444 A1    Apr. 24, 2014

Related U.S. Application Data

(63) Continuation of application No. PCT/JP2013/063533, filed on May 15, 2013.

(30) Foreign Application Priority Data

Jun. 11, 2012 (JP) ................ 2012-131600

(51) Int. Cl.
*A61B 6/00* (2006.01)

(52) U.S. Cl.
CPC ............. *A61B 6/547* (2013.01); *A61B 6/4441* (2013.01); *A61B 6/465* (2013.01); *A61B 6/468* (2013.01)

(58) Field of Classification Search
CPC ......... A61B 6/468; A61B 6/504; A61B 6/547; A61B 6/4441; A61B 6/46; A61B 6/461; A61B 6/465; H01J 2237/24578
See application file for complete search history.

(56) References Cited

U.S. PATENT DOCUMENTS

2004/0202277 A1* 10/2004 Okumura ............... A61B 6/032
  378/16
2005/0089143 A1  4/2005 Nakano et al.
(Continued)

FOREIGN PATENT DOCUMENTS

CN  1535658 A  10/2004
CN  1606963 A  4/2005
(Continued)

OTHER PUBLICATIONS

Combined Chinese Office Action issued Apr. 15, 2015 in Patent Application No. 201380001317.0 (with English language translation of categories of cited documents).

(Continued)

*Primary Examiner* — Thomas R Artman
(74) *Attorney, Agent, or Firm* — Oblon, McClelland, Maier & Neustadt, L.L.P.

(57) ABSTRACT

In an embodiment, an X-ray diagnostic apparatus includes an image capturing unit which captures an X-ray image of a subject on a tabletop, a movement mechanism which moves the tabletop and the image capturing unit relative to each other, an acquisition unit which acquires device position information on the tabletop and the image capturing unit in capturing the X-ray image, a display unit which displays the X-ray image captured by the image capturing unit, an input unit which inputs added information to be added to the X-ray image displayed on the display unit, and a management unit which manages the X-ray image captured by the image capturing unit, the device position information acquired by the acquisition unit, and the added information inputted by the input unit in association with one another.

8 Claims, 3 Drawing Sheets

| MASK IMAGE | ANNOTATION INFORMATION | DEVICE POSITION INFORMATION |
|---|---|---|
| A | MARK A and NOTE A | a1, a2 ··· |
| B | MARK B and NOTE B | b1, b2 ··· |
| ····· | ····· | ····· |

(56) References Cited

U.S. PATENT DOCUMENTS

| | | | |
|---|---|---|---|
| 2006/0184006 A1* | 8/2006 | Chen | A61B 6/12 600/416 |
| 2006/0215817 A1 | 9/2006 | Watanabe | |
| 2007/0058781 A1 | 3/2007 | Nakano et al. | |
| 2007/0118384 A1* | 5/2007 | Gustafson | A61B 6/468 704/275 |
| 2007/0237375 A1 | 10/2007 | Yamagishi et al. | |
| 2008/0212855 A1 | 9/2008 | Shibuya et al. | |
| 2010/0049314 A1* | 2/2010 | Kim | A61F 2/2451 623/2.37 |
| 2011/0131528 A1* | 6/2011 | Nakamura | A61B 6/032 715/810 |
| 2014/0112444 A1* | 4/2014 | Imagawa | A61B 6/4441 378/62 |

FOREIGN PATENT DOCUMENTS

| | | |
|---|---|---|
| CN | 1846615 A | 10/2006 |
| CN | 101040801 A | 9/2007 |
| CN | 101254135 A | 9/2008 |
| JP | 1-181846 A | 7/1989 |
| JP | 7-323035 | 12/1995 |
| JP | 2001-104295 A | 4/2001 |
| JP | 2003-265449 A | 9/2003 |
| JP | 2005-87633 A | 4/2005 |
| JP | 2005-137798 A | 6/2005 |
| JP | 2006-262989 A | 10/2006 |
| JP | 2006-314704 A | 11/2006 |
| JP | 2008-29401 A | 2/2008 |
| JP | 2010-240253 A | 10/2010 |
| JP | 2012-75645 A | 4/2012 |

OTHER PUBLICATIONS

Combined Office Action and Search Report issued Jan. 27, 2016 in Chinese Patent Application No. 201380001317.0 (with English Translation of Category of Cited Documents).

International Search Report issued Jul. 2, 2013 in PCT/JP2013/063533 (with English translation of categories of cited documents).

Office Action issued Oct. 4, 2016, in Japanese Patent Application No. 2012-131600.

* cited by examiner

FIG.3

MASK IMAGE A

NOTE A
MARK A

FIG.4

MASK IMAGE B

NOTE B
MARK B

FIG.5

| MASK IMAGE | ANNOTATION INFORMATION | DEVICE POSITION INFORMATION |
|---|---|---|
| A | MARK A and NOTE A | a1, a2 ⋯ |
| B | MARK B and NOTE B | b1, b2 ⋯ |
| ⋯⋯ | ⋯⋯ | ⋯⋯ |

X-RAY DIAGNOSTIC APPARATUS

CROSS-REFERENCE TO THE RELATED APPLICATION

This application is based on and claims the benefit of priority from International Application No. PCT/JP2013/063533, filed on May 15, 2013 and Japanese Patent Application No. 2012-131600, filed on Jun. 11, 2012; the entire contents of which are incorporated herein by reference.

FIELD

Embodiments described herein relate generally to an X-ray diagnostic apparatus.

BACKGROUND

An X-ray diagnostic apparatus is an apparatus configured to acquire an X-ray image of a subject such as a patient by: irradiating the subject with X-rays from an X-ray irradiation unit; and detecting the X-rays that pass through the subject by use of an X-ray detector. As the X-ray diagnostic apparatus of this type, for example, there has been developed an X-ray diagnostic apparatus provided with a C-arm or the like which holds the X-ray irradiation unit and the X-ray detector in an opposed fashion, and configured to move the X-ray irradiation unit and the X-ray detector to image capturing positions for the subject on a bed, to capture an X-ray image of a region of attention of the subject, and to display the image on a monitor.

The X-ray diagnostic apparatus has a normal image capturing mode, and an X-ray irradiation mode called a fluoroscopic mode designed to consecutively display X-ray images of the subject by consecutively emitting small amounts of X-rays from the X-ray irradiation unit. X-ray images captured in the fluoroscopic mode are generally referred to as fluoroscopic images. In particular, a proposal has been made on a technique (for example, a spot imaging method) of: setting a region of interest (ROI) in a mask image which is an X-ray image; acquiring fluoroscopic images (moving images) of the region of interest by irradiating only the set region of interest with X-rays; and displaying the moving images superimposed on the mask image (still image).

The X-ray diagnostic apparatus capable of capturing the fluoroscopic images as described above is used, for example, for treating an aneurysm. An example of the aneurysm treatment is a stent-graft placement method under X-ray fluoroscopy. In the stent-graft placement method, a surgeon in an operation identifies positions and the like of branching blood vessels prior to the placement of the stent graft. To this end, the surgeon attaches a transparent sheet onto a monitor screen which is displaying the fluoroscopic images, and handwrites marks on the transparent sheet with a pen or the like.

However, when the marks are handwritten on the transparent sheet on the monitor screen as described above, the marks become useless if the image capturing position is changed. For this reason, checking from multiple image capturing positions (image capturing angles, for example) requires a troublesome task to attach another transparent sheet and handwrite marks thereon each time the image capturing position is changed. On the other hand, in the case of employing fluoroscopic road-mapping to superimpose fluoroscopic images in real time, the above-mentioned troublesome task is required again and again for checking from multiple angles.

DETAILED DESCRIPTION

In one embodiment, an X-ray diagnostic apparatus includes: an image capturing unit configured to capture an X-ray image of a subject on a tabletop; a movement mechanism configured to move the tabletop and the image capturing unit relative to each other; an acquisition unit configured to acquire device position information on the tabletop and the image capturing unit in capturing the X-ray image; a display unit configured to display the X-ray image captured by the image capturing unit; an input unit configured to input added information to be added to the X-ray image displayed on the display unit; and a management unit configured to manage the X-ray image captured by the image capturing unit, the device position information acquired by the acquisition unit, and the added information inputted by the input unit while associating them with one another.

Descriptions will be provided for the embodiment by referring to the drawings.

Figure 1:
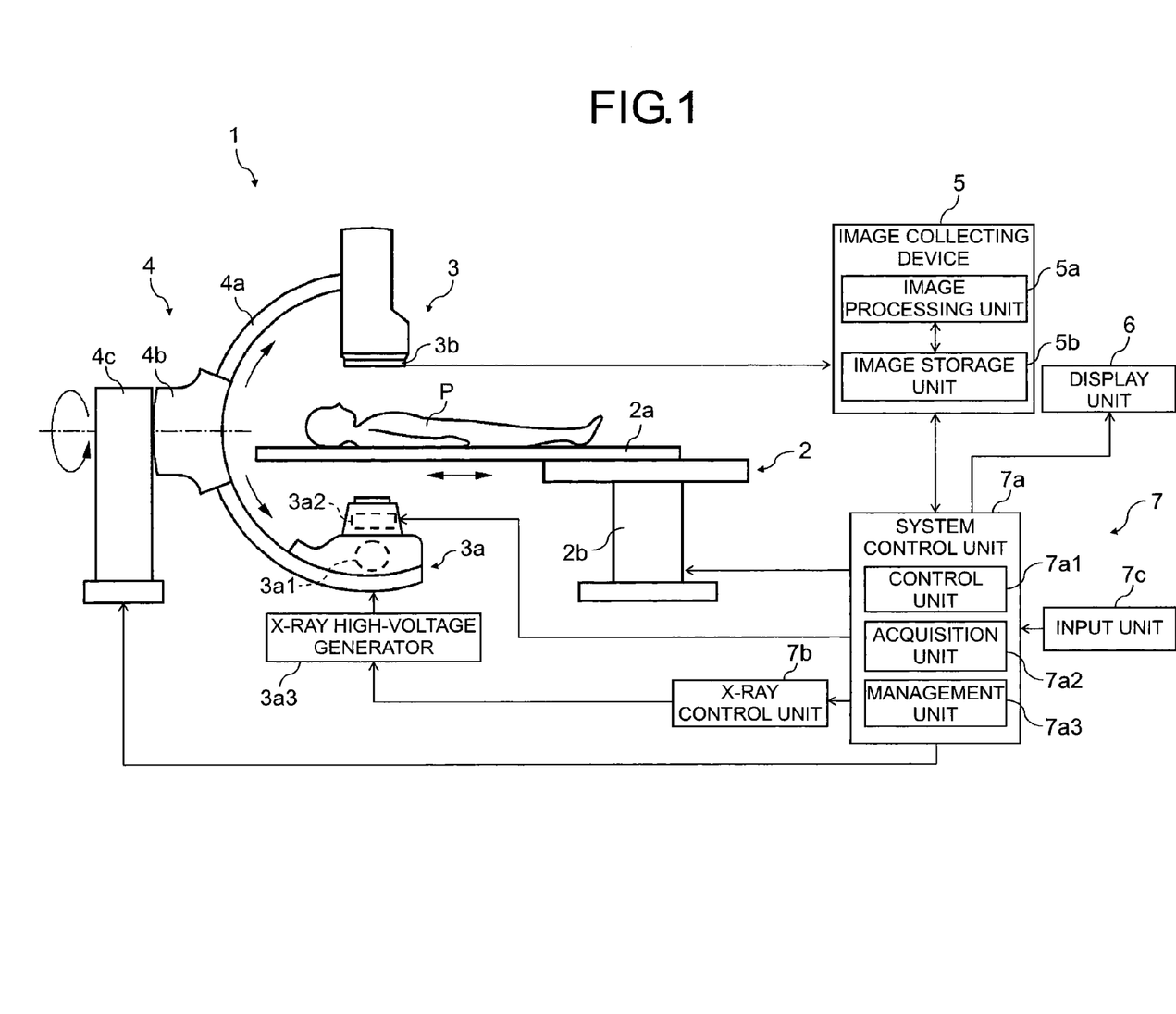
FIG. 1 is a diagram showing a schematic configuration of an X-ray diagnostic apparatus of an embodiment.

As shown in FIG. 1, an X-ray diagnostic apparatus 1 of the embodiment includes: a bed 2 on which to place a subject P such as a patient; an image capturing unit 3 configured to capture an image of the subject P on the bed 2; a holding device 4 configured to hold the image capturing unit 3; an image collecting device 5 configured to collect the X-ray image; the display unit 6 configured to display various images including the X-ray image; and a control device 7 configured to control the units.

The bed 2 includes: a rectangular tabletop 2a on which to place the subject P; and a tabletop driving unit 2b configured to support and move the tabletop 2a in the horizontal direction and in the vertical direction. The tabletop driving unit 2b includes a mechanism configured to move the tabletop 2a, and a driving source used for the movement. The driving source is electrically connected to the control device 7, and its drive is controlled by the control device 7. The bed 2 moves the subject P on the tabletop 2a to a desired position by causing the tabletop driving unit 2b to move the tabletop 2a to a desired height and then to move the tabletop 2a in the horizontal direction. The bed 2 functions as a movement mechanism configured to move the subject P (the tabletop 2a) and the image capturing unit 3 relative to each other.

The image capturing unit 3 includes: an X-ray irradiation unit 3a configured to irradiate the subject P on the tabletop 2a with X-rays, and an X-ray detector 3b configured to detect the X-rays passing through the subject P. The image capturing unit 3 is provided movable around the tabletop 2a, and is configured to capture the X-ray image of the subject P on the tabletop 2a from a desired image capturing position. Examples of the X-ray image include: a fluoroscopic image and a mask image of a region of attention such as the heart.

The X-ray irradiation unit 3a includes: an X-ray tube 3a1 configured to emit X-rays; an X-ray diaphragm 3a2 configured to adjust an irradiation field (irradiation range) of the X-rays emitted from the X-ray tube 3a1 by stopping the X-rays; an X-ray high-voltage generator 3a3 configured to generate a high voltage to be supplied to the X-ray tube 3a1; and so forth. The X-ray irradiation unit 3a supplies the high voltage from the X-ray high-voltage generator 3a3 to the X-ray tube 3a1; causes the X-ray tube 3a1 to emit the X-rays; and irradiates the subject P on the tabletop 2a with the X-rays passing through the X-ray diaphragm 3a3.

In this respect, various types of X-ray diaphragms may be used as the X-ray diaphragm 3a2. For example, an X-ray diaphragm may be used in which: four X-ray blocking members made of lead or the like are arranged in parallel crosses; and the position and size of a window formed by being surrounded by the X-ray blocking members are changed as needed by moving the X-ray blocking members in such a manner as to be brought closer to or be away from each other. The window portion constitutes a passage area where the X-rays pass through, while the X-ray blocking members located around the window constitute a blocking area for absorbing and blocking the X-rays.

The X-ray detector 3b is provided to the holding device 4 while being opposed to the X-ray tube 3a1. The X-ray detector 3b is formed movable in a direction to move closer to or away from the opposed X-ray tube 3a1. The X-ray detector 3b is electrically connected to the control device 7, and transmits a detected X-ray dose, namely, an X-ray image signal to the control device 7. An image intensifier or an X-ray flat panel detector (FPD), for example, may be used as the X-ray detector 3b. Meanwhile, an X-ray flat panel detector of a direct conversion type configured to directly convert X-ray projection information into an electric signal may be used as well.

The holding device 4 includes: a holding arm 4a configured to hold the X-ray tube 3a1 and the X-ray detector 3b in the opposed fashion; an arm supporting unit 4b configured to slidably support the holding arm 4a; and a support column 4c configured to turnably support the arm supporting unit 4b. The holding device 4 includes a mechanism for the movement of the holding device 4, and a driving source for the movement. The driving source is electrically connected to the control device 7, and the drive of the driving source is controlled by the control device 7. The holding device 4 functions as a movement mechanism configured to move the subject P (the tabletop 2a) and the image capturing unit 3 relative to each other.

The holding arm 4a is a C-arm shaped like the letter C, for example. The holding arm 4a is provided to the arm supporting unit 4b in a way that makes the holding arm 4a slidable in the directions of extension of the holding arm. The X-ray tube 3a1 and the X-ray detector 3b are separately provided to the two end portions in the longitudinal direction of the holding arm 4a. In addition, the arm supporting unit 4b slidably holds the holding arm 4a, and is turnably provided to the support column 4c. The support column 4c turnably supports the arm supporting unit 4b, and is installed upright on the floor.

The image collecting device 5 includes: an image processing unit 5a configured to perform a process of generating the X-ray image on the basis of the X-ray dose detected by the X-ray detector 3b; and an image storage unit 5b configured to store the generated X-ray image.

The image processing unit 5a generates the X-ray image of the subject P through a variety of image processing on the basis of the X-ray dose, and transmits the generated X-ray image to the image storage unit 5b. The image storage unit 5b stores the X-ray image transmitted from the image processing unit 5a. A magnetic disk device or a semiconductor disk device (a flash memory), for example, may be used as the image storage unit 5b.

The display unit 6 is a display device configured to display various images, inclusive of the X-ray image transmitted from the image collecting device 5. As the display unit 6, for example, a liquid crystal display, a CRT (cathode ray tube) display, and the like may be used.

The control device 7 includes: a system control unit 7a configured to control the units in the system; an X-ray control unit 7b configured to control the X-ray high-voltage generator 3a3; and an input unit 7c used for an input manipulation by an operator (user) such as a doctor, an assistant, and a technician.

The system control unit 7a controls the units on the basis of various programs and various data which are stored. The system control unit 7a includes, among other things, a control unit 7a1 configured to control the bed 2, the image capturing unit 3, the holding device 4, and the like in response to the input manipulation by the operator with the input unit 7c; an acquisition unit 7a2 configured to acquire device position information on the bed 2 and the holding device 4 (the tabletop 2a and the image capturing unit 3); and a management unit 7a3 configured to manage various sets of information.

The control unit 7a1 controls the movements of the units such as the bed 2, the image capturing unit 3, and the holding device 4, and also controls an aperture value of the X-ray diaphragm 3a2 and display on the display unit 6. For example, in the case where the X-ray image of a region of attention of the subject P is acquired, the control unit 7a1 sets the aperture value of the X-ray diaphragm 3a2 at an appropriate aperture value for capturing the X-ray image of the region of attention.

The acquisition unit 7a2 acquires the device position information on the bed 2, the holding device 4, and the like in capturing the X-ray image. For example, the acquisition unit 7a2 is capable of acquiring the position information on the tabletop 2a on the basis of an output value from a position detection unit (for example, an encoder) provided to the driving source (for example, a servomotor) or the like of the bed 2. In addition, the acquisition unit 7a2 is capable of acquiring the position information (including an arm angle and an arm horizontal position, for example) on the holding arm 4a on the basis of an output value from a position detection unit (for example, an encoder) provided to the driving source (for example, a servomotor) or the like of the holding device 4. Using the position information on the bed 2 and the position information on the holding device 4, the acquisition unit 7a2 is capable of recognizing the positions of the subject P on the tabletop 2a and the image capturing unit 3 relative to each other. Furthermore, the acquisition unit 7a2 is capable of acquiring information on the aperture value of the X-ray diaphragm 3a2 (for example, position information on the X-ray blocking members) on the basis of an output value from a position detection unit (for example, an encoder) provided to the driving source (for example, a servomotor) or the like of the X-ray diaphragm 3a2.

The management unit 7a3 includes a storage unit configured to store various sets of information, and manages a mask image, annotation information, and the device position information while associating them with one another by storing the information in the storage unit. Incidentally, a ROM, a RAM, a magnetic disk device and a semiconductor disk device (a flash memory), for example, may be used as the storage unit.

Here, the annotation information (added information) is supplementary information referring to information in general which can be added to the image. The annotation information is composed of added information having coordinates on a display screen, and added information not having coordinates on the display screen. Examples of the added information having the coordinates on the display screen include: an arrow drawn by the user in order to indicate a specific object; a blood vessel wall handwritten by the user; and notes related thereto. On the other hand, examples of the added information not having the coordinates on the display screen include machine-related information necessary for a fusion with a certain X-ray image (for example, fusion information). Furthermore, examples of the machine-related information include: positions and angles of the holding device 4 and the bed 2 (the tabletop 2a); a source-to-image distance (SID; a distance between the focal point of the X-ray tube and an image reception area); a field of view (FOV); a zoom (a magnification); and the like.

Here, the system control unit 7a outputs various instructions concerning execution of the image processing and the like to the image processing unit 5a of the image collecting devices. In response to the instructions, the image processing unit 5a executes the required processing. The various components including the system control unit 7a and the image processing unit Sa may be formed from hardware including electric circuits. Alternatively, the components may be formed from software including programs for executing these functions. The components may also be formed by combining the hardware and the software.

In accordance with the control by the system control unit 7a, the X-ray control unit 7b controls various conditions including the waveform, namely the amplitude and the pulse width, of the voltage to be applied to the X-ray high-voltage generator 3a3 in order to cause the X-ray tube 3a1 to generate desired X-rays. In response to the control, the X-ray high-voltage generator 3a3 raises and rectifies a voltage, and then supplies the resultant voltage to the X-ray tube 3a1.

The input unit 7c is a manipulation unit configured to receive an input manipulation by the operator such as the doctor, the assistant, and the technician. An input device such as a joystick, a keyboard, a mouse, a footswitch, and a touch panel may be used as the input unit 7c. In one example, the operator moves the image capturing unit 3, namely the X-ray tube 3a1 and the X-ray detector 3b to desired positions by performing the input manipulation with the input unit 7c.

Next, descriptions will be provided for a reproduction process to be performed by the X-ray diagnostic apparatus 1.

Figure 2:
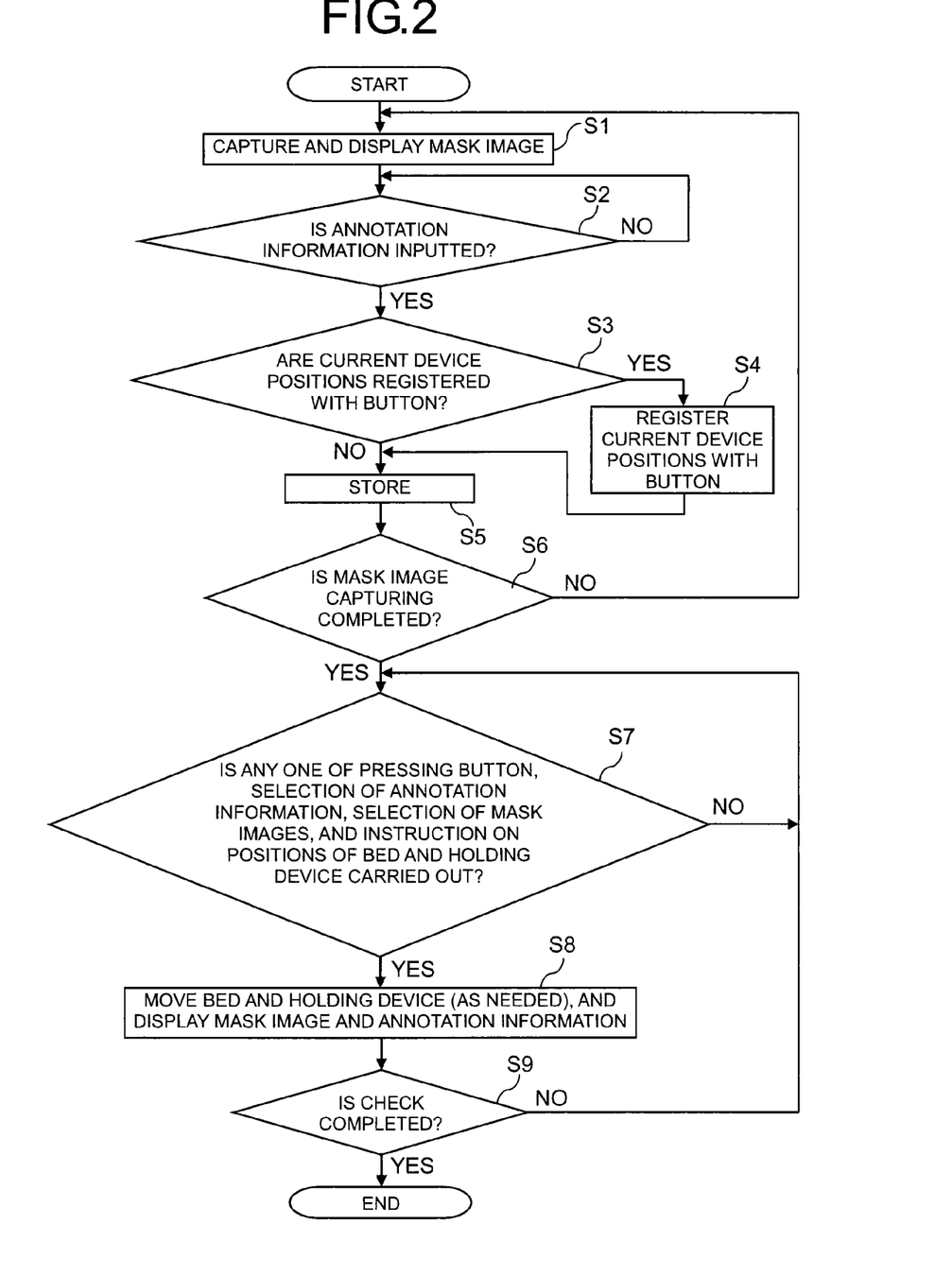
FIG. 2 is a flowchart showing a flow of a reproduction process which is performed by the X-ray diagnostic apparatus shown in FIG. 1.

As shown in FIG. 2, a mask image is captured and displayed on the display unit 6 (step S1). Subsequently, it is judged whether the annotation information is inputted (step S2). This judgment is repeated until the annotation information is inputted (if NO in step S2).

In this respect, the user such as the doctor, the assistant, and the technician inputs the annotation information such as marks and notes by manipulating the input unit 7c such as a mouse, a keyboard, and a touch panel while visually checking the mask image displayed on the display unit 6.

Figure 3:
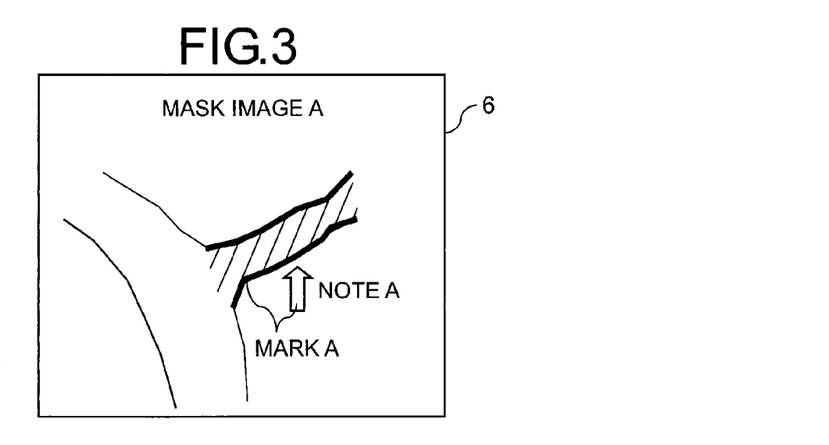
FIG. 3 is an explanatory diagram for explaining an example of a mask image with annotation information (added information).
Figure 4:
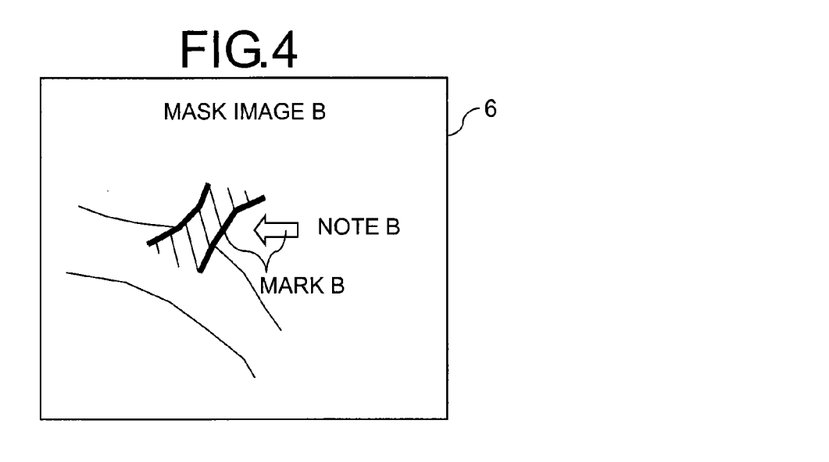
FIG. 4 is an explanatory diagram for explaining another example of a mask image with annotation information.

For example, in the case where a mask image A is displayed on the display unit 6 as shown in FIG. 3, the doctor draws a blood vessel wall (see bold lines in FIG. 3) as a mark A, places an arrow, and writes a note A. Furthermore, in the case where a mask image B (an image captured from an image capturing position which differs from that for capturing the mask image A) is displayed on the display unit 6 as shown in FIG. 4, the doctor similarly draws a blood vessel wall (see bold lines in FIG. 4) as a mark B, places an arrow, and writes a note B. Incidentally, examples of the notes include "the artery can be seen clearly," and "the branching blood vessel can be seen clearly." Notes may be written freely.

If it is judged in step S2 that the annotation information is inputted (if YES in step S2), it is judged whether or not the current device positions should be registered with a button (step S3). In this step, if the user such as the doctor presses the button for instructing the registration, the control unit 7a1 judges that the current device positions should be registered with the button.

If it is judged in step S3 that the current device positions should be registered with the button (if YES in step S3), the current device positions are registered with the button in response to the pressing of the button (step S4). Subsequent, the annotation information, the mask image, and the device position information are associated with one another and are stored in the management unit 7a3 (step S5). On the other hand, if the current device positions should not be registered with the button (if NO in step S3), the annotation information, the mask image, and the device position information are associated with one another without the button registration and are stored in the management unit 7a3 (step S5).

In step 4, if a button such as a function button is pressed by the user such as the doctor, the current device positions are registered with the button, whereby the button and the information on the current device positions are linked to each other. In other words, each combination of the device positions at the time of capturing a mask image is registered with a different button. For example, in the case where a combination of the device positions concerning the mask image A is registered with a button 1, a combination of the device positions concerning the mask image B is registered with a button 2. Thereafter, when the user presses one of the registered buttons, the tabletop 2a and the holding device 4 automatically move to the registered device positions on the basis of the device position information linked to the button.

Figure 5:
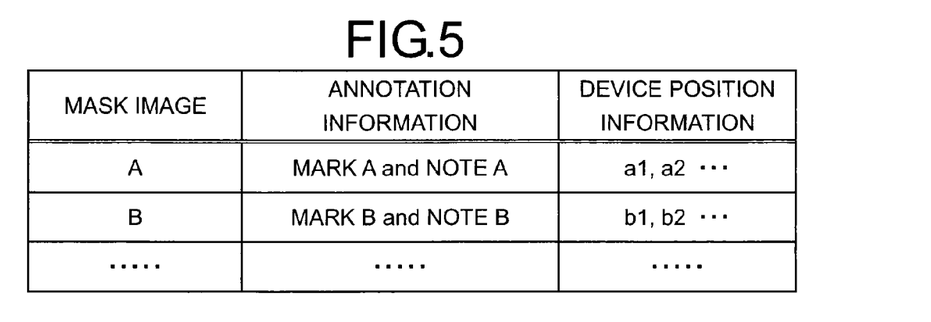
FIG. 5 is an explanatory diagram for explaining storage of the mask images, the annotation information, and device position information.

In step S5, the annotation information is stored in association with the mask image and the device position information. For example, in the case where the annotation information (the mark A and the note A) is written on the mask image A as shown in FIG. 3, the annotation information (the mark A and the note A) is stored as shown in FIG. 5 in association with the mask image A and the device position information (position information a1 on the tabletop 2a, position information a2 on the holding device 4, and the like) obtained in capturing the mask image A. Similarly, in the case where the annotation information (the mark B and the note B) is written on the mask image B as shown in FIG. 4, the annotation information (the mark B and the note B) is stored as shown in FIG. 5 in association with the mask image B and the device position information (position information b1 on the tabletop 2a, position information b2 on the holding device 2, and the like) obtained in capturing the mask image B. Here, examples of the position information include coordinates information representing a two-dimensional position, a three-dimensional position (including an angle), and the like.

After the process in step S5, it is judged whether or not the capturing of the mask image is completed (step S6). In this step, if a button for instructing completion of image capturing is pressed by the user such as the doctor, it is judged that the capturing of the mask is completed. On the other hand, if the button for instructing completion of image capturing is not pressed, but the tabletop 2a and the holding device 4 are moved by manipulation of the input unit 7c, then the capturing of the mask image continues.

If it is judged in step S6 that the capturing of the mask image is not completed (if NO in step S6), the process returns to step S1 where the capturing of the next mask image is started, and hence the above-described steps are repeated. In this way, the annotation information is written on each mask image, and the annotation information is stored while being linked to the mask image and the device position information obtained when the mask image is captured.

On the other hand, if it is judged in step S6 that the capturing of the mask image is completed (if YES in step S6), it is judged whether or not any one of the following actions is carried out, namely, pressing of the button, selection of the annotation information, selection of the mask image, an instruction on the positions of the bed and the holding device (step S7). Now, descriptions will be provided for each of these judgments in turn.

<1. Pressing of Button>

If it is judged in step S7 that the button is pressed (if YES in step S7), the bed 2 and the holding device 4 (the tabletop 2a and the image capturing unit 3) automatically move to their positions registered with the button. In addition, the mask image and the annotation information associated with the device position information are retrieved and displayed on the display unit 6 (step S8).

Upon pressing the button, the user manipulates the input unit 7c such as the mouse and the touch panel, and selects a desired button from the multiple buttons. Here, the device positions are registered with each of the multiple buttons such as function buttons in the above-described step S4.

In this respect, let us assume a case as an example where the device positions when the mask image A is captured are registered with the button 1. In this case, once the button 1 is pressed, the tabletop 2a and the holding device 4 move to their positions based on the device position information (the position information a1 on the tabletop 2a, the position information a2 on the holding device 4, and the like) corresponding to the button 1. Furthermore, the mask image A and the annotation information (the mark A and the note A) associated with the device position information are retrieved from the management unit 7a3 (see FIG. 5) and are displayed on the display unit 6 (see FIG. 3).

In addition, let us assume a case where the device positions when the mask image B is captured are registered with the button 2. In this case, once the button 2 is pressed, the tabletop 2a and the holding device 4 move to their positions based on the device position information (the position information b1 on the tabletop 2a, the position information b2 on the holding device 4, and the like) corresponding to the button 2. Furthermore, the mask B and the annotation information (the mask B and the note B) associated with the device position information are retrieved from the management unit 7a3 (see FIG. 5) and are displayed on the display unit 6 (see FIG. 4). In this way, it is possible to reproduce the device positions and to reproduce the display of the mask image and the annotation information (the mark and the note) only by pressing the corresponding registered button.

<2. Selection of Set of Annotation Information>

Meanwhile, if it is judged in step S7 that any one set of the annotation information is selected (if YES in step S7), the selected set of the annotation information as well as the mask image and the device position information associated with the set of annotation information are retrieved. Thereafter, the bed 2 and the holding device 4 (the tabletop 2a and the image capturing unit 3) automatically move to their positions based on the retrieved device position information. In addition, the mask image and the annotation information thus retrieved are displayed on the display unit 6 (step S8).

Upon selection of the annotation information, the annotation information, or note information, for example, is edited as a list and displayed on the display unit 6 (list display). Here, the list may include not only the notes but also thumbnails of the downsized mask images. The user selects a desired set of the annotation information from the list by manipulating the input unit 7c such as the mouse and the touch panel.

For example, when the note A is selected from the list, the mask image A and the device position information (the position information a1 on the tabletop 2a, the position information a2 on the holding device 4, and the like) associated with the annotation information including the note A are retrieved from the management unit 7a3 (see FIG. 5), and the tabletop 2a and the holding device 4 automatically move to their positions based on the device position information. Furthermore, the annotation information including the selected note A and the retrieved mask image A are displayed on the display unit 6 (see FIG. 3).

On the other hand, when the note B is selected from the list, the mask image B and the device position information (the position information b1 on the tabletop 2a, the position information b2 on the holding device 4, and the like) associated with the of annotation information including the note B are retrieved from the management unit 7a3 (see FIG. 5), and the tabletop 2a and the holding device 4 automatically move to their positions based on the device position information. Furthermore, the annotation information including the selected note B and the retrieved mask image B are displayed on the display unit 6 (see FIG. 4). In this way, it is possible to reproduce the device positions and to reproduce the display of the mask image and the annotation information (the corresponding mark and the note) only by selecting the corresponding annotation information.

<3. Selection of Mask Image>

Meanwhile, if it is judged in step S7 that one of the mask images is selected (if YES in step S7), the selected mask image and the annotation information and device position information associated with the mask image are retrieved. Thereafter, the bed 2 and the holding device 4 (the tabletop 2a and the image capturing unit 3) automatically move to their positions based on the retrieved device position information. Moreover, the retrieved mask image and the annotation information are displayed on the display unit 8 (step S8).

Upon selection of the mask image, the thumbnails of the mask images are displayed on the display unit 6 (thumbnail display). The user selects a desired mask image from the thumbnails by manipulating the input unit 7c such as the mouse and the touch panel. Note that the display in this case is not limited to the thumbnail display.

For example, when the mask image A is selected from the list, the annotation information (the mark A and the note A)

and the device position information (the position information a1 on the tabletop 2a, the position information a2 on the holding device 4, and the like) associated with the mask image A are retrieved from the management unit 7a3 (see FIG. 5), and the tabletop 2a and the holding device 4 automatically move to their positions based on the device position information. Furthermore, the selected mask image A and the retrieved annotation information (the mark A and the note A) are displayed on the display unit 6 (see FIG. 3).

On the other hand, when the mask image B is selected from the list, the annotation information (the mark B and the note B) and the device position information (the position information b1 on the tabletop 2a, the position information b2 on the holding device 4, and the like) associated with the mask image B are retrieved from the management unit 7a3 (see FIG. 5), and the tabletop 2a and the holding device 4 automatically move to their positions based on the device position information. Furthermore, the selected mask image B and the retrieved annotation information (the mark B and the note B) are displayed on the display unit 6 (see FIG. 4). In this way, it is possible to reproduce the device positions and to reproduce the display of the mask image and the annotation information (the mark and the note) only by selecting the corresponding mask image.

<4. Instruction on Positions of Holding Device and Bed>

Besides, if it is judged in step S7 that the positions of the bed 2 and the holding position 4 are instructed (if YES in step S7), the bed 2 and the holding device 4 (the tabletop 2a and the imaging capturing unit 3) automatically move to their positions based on the instructed device position information (automatic positioning). Furthermore, the mask image and the annotation information associated with the device position information are retrieved. The mask image and the annotation information thus retrieved are displayed on the display unit 6 (step S8).

Upon the position instruction, the user specifies an angular position and the like of the holding device 4 by manipulating the input unit 7c such as the mouse and the touch panel. Here, the holding device 4 may be manually moved to the same desired image-capturing position instead of performing the automatic positioning.

For example, when the tabletop 2a and the holding device 4 move to a desired image-capturing position 1, the mask image A and the annotation information (the mark A and the note A) associated with the device position information (the position information a1 on the tabletop 2a, the position information a2 on the holding device 4, and the like) corresponding to the image-capturing position 1 are retrieved from the management unit 7a3 (see FIG. 5) and are displayed on the display unit 6 (see FIG. 3).

Furthermore, when the tabletop 2a and the holding device 4 move to a desired image-capturing position 2, the mask image B and the annotation information (the mark B and the note B) associated with the device position information (the position information b1 on the tabletop 2a, the position information b2 on the holding device 4, and the like) corresponding to the image-capturing position 2 are retrieved from the management unit 7a3 (see FIG. 5) and are displayed on the display unit 6 (see FIG. 4). In this way, it is possible to reproduce the display of the mask image and the annotation information (the mark and the note) only by reproducing the positions of the tabletop 2a and the holding device 4 (image capturing unit 3). In the manual movement mode, when the holding device 4 comes to a position based on the device position information, the mask image and the annotation information corresponding to the position are displayed.

After the above-described process in step S8, it is judged whether or not all the checks are completed (step S9). In this step, if the user such as the doctor presses a button for instructing completion of the checks, it is judged that all the checks are completed. If it is judged that all the checks are completed (if YES in step S9), the process is terminated. On the other hand, if it is judged that the check completion button is not pressed and all the checks are not completed yet (if NO in step S9), the process returns to step S7 and the judgment in step S7 is repeated.

In the reproduction process described above, when any one of the mask image, the annotation information, or the device position information is selected, it is possible to display the corresponding mask image and the corresponding annotation information, as well as to easily reproduce the device positions of the bed 2 and the holding device 4, namely, the tabletop 2a and the image capturing unit 3 located when the mask image was captured. This configuration reduces loads on the user and increases the work efficiency of the user. Accordingly, it is possible to shorten a time needed for a surgical operation. In addition, since the above-described reproduction process facilitates the checks from the multiple positions, it is possible to increase a success rate of stent graft placement. In addition, since the mask images captured from the multiple image capturing positions can accurately be reproduced, it is possible to avoid unnecessary image capturing, and accordingly to reduce an amount of radiation exposure and an amount of use of a contrast medium.

In the foregoing embodiment, as described above, each time an X-ray image of the subject P on the tabletop 2a is captured by the image capturing unit 3, the X-ray image is associated with the device position information on the tabletop 2a and the image capturing unit 3 when the X-ray image is captured, and the annotation information (added information) added to the X-ray image. Then, the X-ray image, the device position information, and the annotation information thus associated are managed by the management unit 7a3. Thereby, the multiple X-ray images, the multiple sets of device position information, and the multiple sets of annotation information are managed while being associated with one another. For this reason, when any one of the X-ray images, any one of the sets of device position information, or any one of the sets of annotation information is selected, the rest of the information corresponding thereto can be retrieved from the management unit 7a3 for use. In other words, the selection of any one of the above-mentioned information makes it possible to display the X-ray image and the annotation information corresponding thereto, and to easily reproduce the corresponding device positions of the tabletop 2a and the image capturing unit 3 located when the X-ray image was captured. Accordingly, it is possible to increase the work efficiency of the user.

In addition, in displaying any one of the sets of annotation information on the display unit 6, the control unit 7a1 performs the process for moving the tabletop 2a and the image capturing unit 3 to the positions based on the device position information associated with the to-be-displayed annotation information by use of the movement mechanism (the bed 2 and the holding device 4), and the process for displaying the X-ray image associated with the to-be-displayed annotation information together with the annotation information on the display unit 6. Thus, by only selecting the annotation information, it is possible to display the annotation information and the X-ray image associated therewith, and to easily reproduce the device positions of the tabletop 2a and the image capturing unit 3 located when the X-ray image was captured.

Furthermore, in displaying the X-ray image on the display unit 6, the control unit 7a1 performs: the process for moving the tabletop 2a and the image capturing unit 3, by use of the movement mechanism (including the bed 2 and the holding device 4), to the relative positions based on the device position information associated with the X-ray image to be displayed; and the process for displaying the to-be-displayed X-ray image and the annotation information associated with the to-be-displayed X-ray image on the display unit 6. Thereby, it is possible to display the X-ray image and the annotation information associated thereto, and to easily reproduce the device positions of the tabletop 2a and the image capturing unit 3 located when the X-ray image was captured only by selecting the corresponding X-ray image.

Moreover, when the tabletop 2a and the image capturing unit 3 are moved by the movement mechanism (the bed 2 and the holding unit 4) to the relative positions based on the device position information, the control unit 7a1 performs the process for displaying the X-ray image and the annotation information associated with the device position information on the display unit 6. Thereby, it is possible to easily reproduce the display of the X-ray image and the annotation information associated with the positions of the tabletop 2a and the holding device 4 only by reproducing the positions.

It should be noted that the annotation information added to the X-ray image is not limited to the annotation information to be directly added to the relevant X-ray image, but it is also possible to associate the X-ray image with annotation information to be added to another image. For example, an X-ray image, annotation information (fusion information) to be added to another CT image, and the angular position of the holding device 4 are associated with one another. The X-ray image is aligned with the CT image a at an angle a, and is fused with the CT image. Thereafter, if the angle a is changed to an angle b, the fusion of the X-ray image and the CT image is cancelled at that point. If the angle b is returned to the angle a, the X-ray image is automatically fused with the CT image again.

What is more, in the case where a display condition of an X-ray image displayed on the display unit 6 is changed, a display condition of the annotation information displayed by being superimposed onto the X-ray image may be changed in accordance with the change in the display condition of the X-ray image. In this case, for example, the display of the annotation information is changed in accordance with the change in the display condition such as a zoom condition. Thereby, the display condition of the annotation information displayed by being superimposed onto the fluoroscopic image as the X-ray image follows a change in the zoom condition, the field of view (FOV), and the like. For this reason, the annotation information can be continuously displayed in an easily visible condition and in the right place.

Furthermore, a process may be performed for: displaying a fluoroscopic image captured by the image capturing unit 3 and annotation information on the display unit 6 in a superimposed manner; and displaying a mask image associated with the to-be-displayed annotation information and the fluoroscopic image captured by the image capturing unit 3 on the display unit 6 in a superimposed manner. Thereby, the user such as the doctor can cause the display unit 6 to display a first image including the fluoroscopic image and the annotation information, and a second image including the fluoroscopic image and the mask image (fluoroscopic road-mapping display) at the same time. Instead, two display units 6 may be provided to display the first image and the second image independently on the two display units 6.

Moreover, a process may be performed for causing the display unit 6 to display a fusion image of an X-ray image captured by the image capturing unit 3 and a CT image, by fusing them by use of the device position information associated with the captured X-ray image and fusion information on the CT image. Thereby, the user such as the doctor can cause the display unit 6 to display the fusion image of the X-ray image and the CT image.

In addition, the X-ray image captured by the image capturing unit 3 may be fused with an image such as an MRI image, a PET image, and an ultrasonogram.

While certain embodiments have been described, these embodiments have been presented by way of example only, and are not intended to limit the scope of the inventions. Indeed, the novel embodiments described herein may be embodied in a variety of other forms; furthermore, various omissions, substitutions and changes in the form of the embodiments described herein may be made without departing from the spirit of the inventions. The accompanying claims and their equivalents are intended to cover such forms or modifications as would fall within the scope and spirit of the inventions.

What is claimed is:

1. An X-ray diagnostic apparatus comprising:
an image capturing unit configured to capture an X-ray image of a subject on a tabletop;
a movement mechanism configured to move the tabletop and the image capturing unit relative to each other;
an acquisition unit configured to acquire device position information on the tabletop and the image capturing unit in capturing the X-ray image;
a display unit configured to display the X-ray image captured by the image capturing unit;
an input unit configured to input added information to be added to the X-ray image displayed on the display unit; and
a management unit configured to manage the X-ray image captured by the image capturing unit, the device position information acquired by the acquisition unit, and the added information inputted by the input unit in association with one another, wherein
the input unit is further configured to receive manipulation for selecting the added information without selecting the X-ray image or the device position information displayed on the display unit.

2. The X-ray diagnostic apparatus of claim 1, further comprising:
a control unit configured to, when the added information managed by the management unit is selected on the display unit, perform a process for causing the movement mechanism to move the tabletop and the image capturing unit relative to each other to positions based on the device position information associated with the to-be-displayed added information, and perform a process for causing the display unit to display the X-ray image associated with the to-be-displayed added information together with the to-be-displayed added information.

3. The X-ray diagnostic apparatus of claim 1, further comprising:
a control unit configured to, when the X-ray image managed by the management unit is selected, perform a process for causing the movement mechanism to move the tabletop and the image capturing unit relative to each other to positions based on the device position information associated with the to-be-displayed X-ray image, and perform a process for causing the display unit to display the to-be-displayed X-ray image together with the added information associated with the to-be-displayed X-ray image.

4. The X-ray diagnostic apparatus of claim 1, further comprising:
a control unit configured to perform a process for causing the display device to display the X-ray image and the added information both associated with the device position information when the movement mechanism moves the tabletop and the image capturing unit relative to each other to positions based on the device position information.

5. The X-ray diagnostic apparatus of claim 1, further comprising:
a control unit configured to, when a display condition of the X-ray image displayed on the display unit changes, perform a process for changing a display condition of the added information displayed on the display unit in accordance with the change in the display condition of the X-ray image.

6. The X-ray diagnostic apparatus of claim 1, wherein the image capturing unit is capable of capturing a mask image and a fluoroscopic image as the X-ray image, the acquisition unit acquires the device position information on the tabletop and the image capturing unit in capturing the mask image,
the display unit displays the mask image captured by the image capturing unit,
the input unit inputs the added information to be added to the mask image displayed on the display unit,
the management unit manages the mask image captured by the image capturing unit, the device position information acquired by the acquisition unit, and the added information inputted by the input unit in association with one another, and
the X-ray diagnostic apparatus further comprises a control unit configured to perform a process for causing the display unit to display the fluoroscopic image captured by the image capturing unit and the added information in a superimposed manner, and to perform a process for causing the display unit to display the mask image associated with the to-be-displayed added information and the fluoroscopic image captured by the image capturing unit in a superimposed manner.

7. The X-ray diagnostic apparatus of claim 1, wherein the added information includes coordinates information.

8. The X-ray diagnostic apparatus of claim 1, wherein the added information includes text information.

* * * * *